US006402678B1

(12) United States Patent
Fischell et al.

(10) Patent No.: US 6,402,678 B1
(45) Date of Patent: Jun. 11, 2002

(54) MEANS AND METHOD FOR THE TREATMENT OF MIGRAINE HEADACHES

(75) Inventors: Robert E. Fischell, Dayton, MD (US); David R. Fischell, Fair Haven, NJ (US); Adrian R. M. Upton, Dundas (CA)

(73) Assignee: NeuraLieve, Inc., Glenelg, MD (US)

( * ) Notice: Subject to any disclaimer, the term of this patent is extended or adjusted under 35 U.S.C. 154(b) by 14 days.

(21) Appl. No.: 09/629,210

(22) Filed: Jul. 31, 2000

(51) Int. Cl.⁷ ................................................. A61N 2/04
(52) U.S. Cl. ....................................................... 600/13
(58) Field of Search ........................................ 600/9–15

(56) References Cited

U.S. PATENT DOCUMENTS

| | | | |
|---|---|---|---|
| 4,305,402 A | | 12/1981 | Katims |
| 4,646,744 A | | 3/1987 | Capel |
| 4,674,482 A | * | 6/1987 | Waltonen et al. .............. 600/14 |
| 4,844,075 A | | 7/1989 | Liss |
| 4,940,453 A | * | 7/1990 | Cadwell ....................... 600/13 |
| 4,994,016 A | | 2/1991 | Atwood |
| 5,078,674 A | * | 1/1992 | Cadwell ....................... 600/13 |
| 5,084,007 A | | 1/1992 | Malin et al. |
| 5,116,304 A | * | 5/1992 | Cadwell ....................... 600/13 |
| 5,215,086 A | | 6/1993 | Terry et al. |
| 5,421,817 A | | 6/1995 | Liss et al. |
| 5,540,734 A | | 7/1996 | Zabara |
| 5,707,334 A | * | 1/1998 | Young ............................ 600/9 |
| 5,725,471 A | * | 3/1998 | Davey et al. .................. 600/13 |
| 5,738,625 A | * | 4/1998 | Gluck ............................ 600/9 |
| 5,769,778 A | * | 6/1998 | Abrams et al. ................ 600/14 |
| 5,782,874 A | | 7/1998 | Loos |
| 5,800,459 A | | 9/1998 | Spano et al. |
| 6,016,449 A | | 1/2000 | Fischell et al. |
| 6,042,531 A | * | 3/2000 | Holcomb ....................... 600/13 |
| 6,099,459 A | * | 8/2000 | Jacobson ....................... 600/13 |
| 6,123,658 A | * | 9/2000 | Schweighofer et al. ....... 600/13 |
| 6,128,538 A | | 10/2000 | Fischell et al. |
| 6,132,361 A | * | 10/2000 | Epstein et al. ................ 600/13 |
| 6,134,474 A | | 10/2000 | Fischell et al. |
| 6,162,166 A | * | 12/2000 | Nuewirth ...................... 600/14 |
| 6,266,556 B1 | * | 7/2001 | Ives et al. .................. 600/13 X |

OTHER PUBLICATIONS

S.L. Bridgers, "The Safety of Transcranial Magnetic Stimulation Reconsidered: Evidence Regarding Cognitive and Other Cerebral Effects," Magnetic Motor Stimulation: Basic Principles and Clinical Experience (EEG Suppl. 43) 1991, pp. 170–179.

P. Jennum et al., "Transcranial magnetic stimulation. Its role in the evaluation of patients with partial epilepsy," Acta Neurol. Scand. 1994: Suppl. 152, pp. 93–96.

A. Pascual–Leone et al., "Akinesia in Parkinson's Disease," Neurology 44, May 1994, pp. 884–891.

(List continued on next page.)

*Primary Examiner*—Eric F. Winakur
*Assistant Examiner*—Joseph A Cadugan

(57) ABSTRACT

Disclosed is a means and method for the treatment of migraine headaches. Patients who have migraine headaches typically have a band of excited brain neurons that are a precursor of the headache. By placing an intense alternating magnetic field onto a certain region of the brain, an electrical current can be generated in the cerebral cortex that can depolarize these excited brain neurons. This procedure can stop a migraine headache in some patients or at least decrease its severity. The device to perform this function can be called a "magnetic depolarizer". The magnetic depolarizer can be placed in some headgear such as a bicycle helmet in order to place the magnetic field at the correct location relative to the patient's cerebral cortex. This technique can be particularly valuable for patients who have a perceptible aura that occurs prior to the onset of a migraine headache. A visual aura caused by the progression of an excited band of neurons in a patient's occipital lobe, which aura occurs 20 to 30 minutes prior to the onset of head pain, would be particularly well treated by means of the magnetic depolarizer.

25 Claims, 4 Drawing Sheets

OTHER PUBLICATIONS

J. Classen et al., "Epileptic seizures triggered directly by focal transcranial magnetic stimulation," Electroencephalography and Clinical Neurophysiology 94 (1995), pp. 19–25.

K. Migita et al., "Transcranial Magnetic Coil Stimulation of Motor Cortex in Patients with Central Pain," Neurosurgery, vol. 36, No. 5, May 1995, pp. 1037–1040.

H. Wang et al., "LTD and LTP induced by transcranial magnetic stimulation in auditory cortex," Neuroreport 7 (1996), pp. 521–525.

R. Chen et al., "Safety of different inter–train intervals for repetetive transcranial magnetic stimulation and recommendations for safe ranges of stimulation parameters," Electroencephalography and Clinical Neurophysiology 105 (1997), pp. 415–421.

E.M. Wassermann, "Risk and Safety of Repetitive Transcranial Magnetic Stimulation: Report and Suggested Guidelines from the International Workshop on the Safety of Repetitive Transcranial Mag. Stim . . . ," Electroenceph. and Clin. Neurophys. 108 (1998), pp. 1–16.

S.K. Aurora et al., "Brain excitability in migraine: evidence from transcranial magnetic stimulation studies," Current Opinion in Neurology, 1998, 11, pp. 205–209.

G.J. Ettinger, et al., "Experimentation with a transcranial magnetic stimulation system for functional brain mapping," Medical Image Analysis (1998) vol. 2, No. 2, pp. 133–142.

A. Schulze–Bonhage et al., "Safety of single and repetitive focal transcranial magnetic stimuli as assessed by intracranial EEG recordings in patients with partial epilepsy," J. Neurol. (1999) 246, pp. 914–919.

A. Maertens De Noordhout et al., "Transcranial magnetic stimulation in migraine," Transcranial Magnetic Stimulation (EEG Suppl. 51), 1999, pp. 260–264.

R.A.L. MacDonell et al., "Motor cortex localization using functional MRI and transcranial magnetic stimulation," Neurology 1999;53, pp. 1462–1467.

M. Hallett, "Transcranial magnetic stimulation and the human brain," Nature, vol. 406, Jul. 13, 2000, pp. 147–150.

* cited by examiner

MEANS AND METHOD FOR THE TREATMENT OF MIGRAINE HEADACHES

BACKGROUND OF THE INVENTION

Migraine headaches occur in approximately 12% of the world population. Therefore, in the United States in the year 2000 there are approximately 30 million people who suffer from this affliction. Although medicines have been created that significantly diminish the suffering of migraine patients, the medicines often have highly undesirable side effects and many patients do not obtain satisfactory relief from the severe headache pain and other discomforts associated with migraine. Furthermore, migraine headaches are typically treated after they have become painful, i.e., the treatment is often ineffective in preventing the onset of the migraine headache. Other than some drugs for some patients, there is no known treatment for migraine headaches that can be applied after a patient detects an aura of that headache to prevent the occurrence of pain and other undesirable manifestations of that migraine headache. A non-invasive, non-drug method for preventing the occurrence of migraine headaches would be a remarkable boon for those millions of people all over the world who suffer from these painful experiences.

In 1985, A. T. Barker, et al (Lancet, 1985, pp. 1105–1107) described the use of a coil placed over the scalp which produced a high intensity, time varying, magnetic field. This magnetic field produces an electric current in the cortex of the human brain which can in turn produce certain effects on brain neurons. By the year 2000, this type of system was given the name Transcranial Magnetic Stimulation (TMS). If repetitive magnetic pulses are applied in this manner, it has been given the name rTMS.

In the journal Neurology (Apr. 11, 2000, pp. 1529–1531) it has been reported by B. Boroojerdi, et al that rTMS at a rate of one pulse per second can create a reduction of the excitability of the neurons of the human visual cortex. However, no prior art has indicated that rTMS can be used for the preventing the occurrence of migraine headaches.

SUMMARY OF THE INVENTION

This invention is a means and method for the treatment of migraine headaches for those patients who experience a distinct aura before the actual occurrence of the symptoms of the migraine headache. It is estimated that approximately 40% of all migraine patients have a distinct aura that is a precursor of a migraine headache. Approximately half of these patients have a visual aura that typically begins as a small pattern of scintillating colored lights that have the appearance of wiggling worms. Over a time period of between 20 and 30 minutes, the pattern enlarges until it occupies nearly the entire visual field. During this time period, the patient might also completely lose part of his visual field. At the end of this visual aura, most migraine patients have a severe headache that is often accompanied by other symptoms such as nausea, vomiting and other unpleasant feelings. Many migraine patients who don't have a visual aura have some other precursor of a migraine that can be perceived from minutes to hours before the actual start of the headache.

The visual aura is a result of the spatial progression of a band of brain cells that are excited in that band across one half of the brain's occipital lobe. This band moves in an anterior direction at the rate of approximately 2–5 mm per minute. It is this excited band of neurons of the brain that produces the scintillating colored lights that are perceived by the patient as an aura that is a precursor of a migraine headache. Behind this leading band of excited neurons, a spreading region of neurons with depressed electrical excitability occurs. This phenomenon is known as "the spreading depression of Leao".

It is believed that if the advancing band of excited neurons can be stopped before the aura has completed its 20 to 30 minute time duration period, the migraine headache will not occur. One way to stop such an advancing band of excited brain neurons would be by imposing a high enough electric current through these neurons so that they become depolarized. This could be accomplished by means of electrodes placed on the brain's surface at the occipital lobe (i.e., the visual cortex). If these electrodes would have at least several milliamps of electrical current placed across them, the excited neurons could be depolarized, thus eliminating their enhanced excitability. However, this would require surgery to implant such electrodes. Also, a neurostimulator attached by wires to the electrodes would be required, which neurostimulator would be adapted to place a voltage across the electrodes to cause the flow of a sufficiently high electrical current to depolarize the advancing band of excited neurons.

The invention disclosed herein is a non-invasive, externally applied device that is placed on or near the patient's head in the region of the brain where the aura originates (e.g., the occipital lobe) as soon as possible after the patient becomes aware of a visual (or any other type) aura that is a precursor of the migraine headache. For patients whose aura originates from a region of the cerebral cortex that is not the occipital lobe, the depolarizing device can be applied to that region of the brain. By the use of a high intensity alternating magnetic field, a sufficiently high electrical current can be placed onto the advancing band of excited neurons so as to depolarize those neurons thereby terminating the aura before it is able to progress into a migraine headache. Depolarization of neurons in advance of the advancing band of excited neurons may also be used to prevent a migraine headache. This is because depolarized neurons become refractory after rTMS is applied. This is analogous to cutting down or burning the trees in front of a forest fire in order to prevent the spread of that forest fire.

The one pulse per second of rTMS described by Boroojerdi, et al, which was proven to cause a reduction of cerebral cortex excitability, could be applied to break up the advancing band of excited neurons that is the cause of the visible aura of a migraine headache. Since an aura has a time duration that is typically at least 20 minutes, the patient has a sufficient time period for placing the rTMS magnetic depolarizer in the appropriate position for it to be effective in depolarizing the advancing band of excited brain neurons.

It should also be noted that stimulation of the scalp might also have an effect in preventing or decreasing the severity of a migraine headache for at least some patients. Scalp stimulation may act as a conditioning, response that becomes associated with the migraine process. Pairing this response with rTMS may provide cessation of the migraine process with progressively less intensity of magnetic stimulation.

Since the band of excited neurons that create a visual aura moves from the back of the head in an anterior direction, and since either the left or right half of the occipital lobe might be involved, the magnetic depolarizer would optimally be placed along the posterior-anterior centerline at the top of the head. If it is known that a particular patient has the spreading depression on either the right or the left half of the occipital lobe, then the magnetic depolarizer might be placed only on that region where the spreading depression occurs. If the aura originates from a part of the cerebral cortex that is not the occipital lobe, then the alternating magnetic field can be appropriately placed to depolarize neurons in that location. It is expected that the patient can be trained to recognize the symptoms from a particular area of the brain so that the magnetic depolarizer can be placed in an optimum location to prevent the occurrence of a migraine headache.

The magnetic depolarizer can be formed in a race-track, figure-eight shape with its long axis placed along the head's posterior-anterior centerline. The width of the magnetic depolarizer might be between 1 and 10 cm and its height in a direction above the skull could be between 0.5 to 5 cm. The length of magnetic depolarizer would typically be between 3 and 15 cm. The magnetic depolarizer could be placed within some form of head covering such as a bicycle helmet. A rechargeable battery and electronic circuitry to generate the required alternating magnetic field could also be contained within a helmet type of head gear. A conventional A-C adapter (recharging device) could be provided to the patient for recharging the battery of the magnetic depolarizer system.

A sufficiently intense alternating magnetic field must be created that would cause the excited band of brain neurons to be depolarized before this band has a chance to create a migraine headache. The intensity of the magnetic field at the surface of the brain should be between 0.1 and 10 Tesla. The frequency rate of the magnetic pulses should be between 0.1 Hz and 1.0 kHz. With some patients a single, short duration pulse may be all that is required to stop an advancing band of excited neurons from proceeding to a full-blown migraine headache. The magnetic pulses can be applied continuously for a period of between 0.1 and 100 seconds. By applying a time varying magnetic field to the neurons of the cerebral cortex (and also to the neurons in the scalp), a patient could be able to actually prevent the occurrence of a migraine headache.

Thus, an objective of this invention is to prevent the occurrence of a migraine headache by creating a high intensity, time varying magnetic field by means of a magnetic depolarizer placed onto the scalp of a patient who has an aura which is a precursor of a migraine headache, the magnetic depolarizer being adapted to cause depolarization of the neurons in the cerebral cortex where the aura originates.

Another object of this invention is to have the magnetic depolarizer placed inside a headgear that the patient can place on his or her head, the headgear being adapted to place the magnetic depolarizer at a specific location relative to the patient's cerebral cortex.

Still another object of the invention is to have a magnetic depolarizer system that includes a battery, electronic circuitry (including a magnetic depolarizer) for creating a high intensity, time varying magnetic field, a patient operated ON-OFF switch and settings of the system's operating parameters that are set by a physician.

Still another object of the invention is to have the magnetic depolarizer system use a rechargeable battery.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
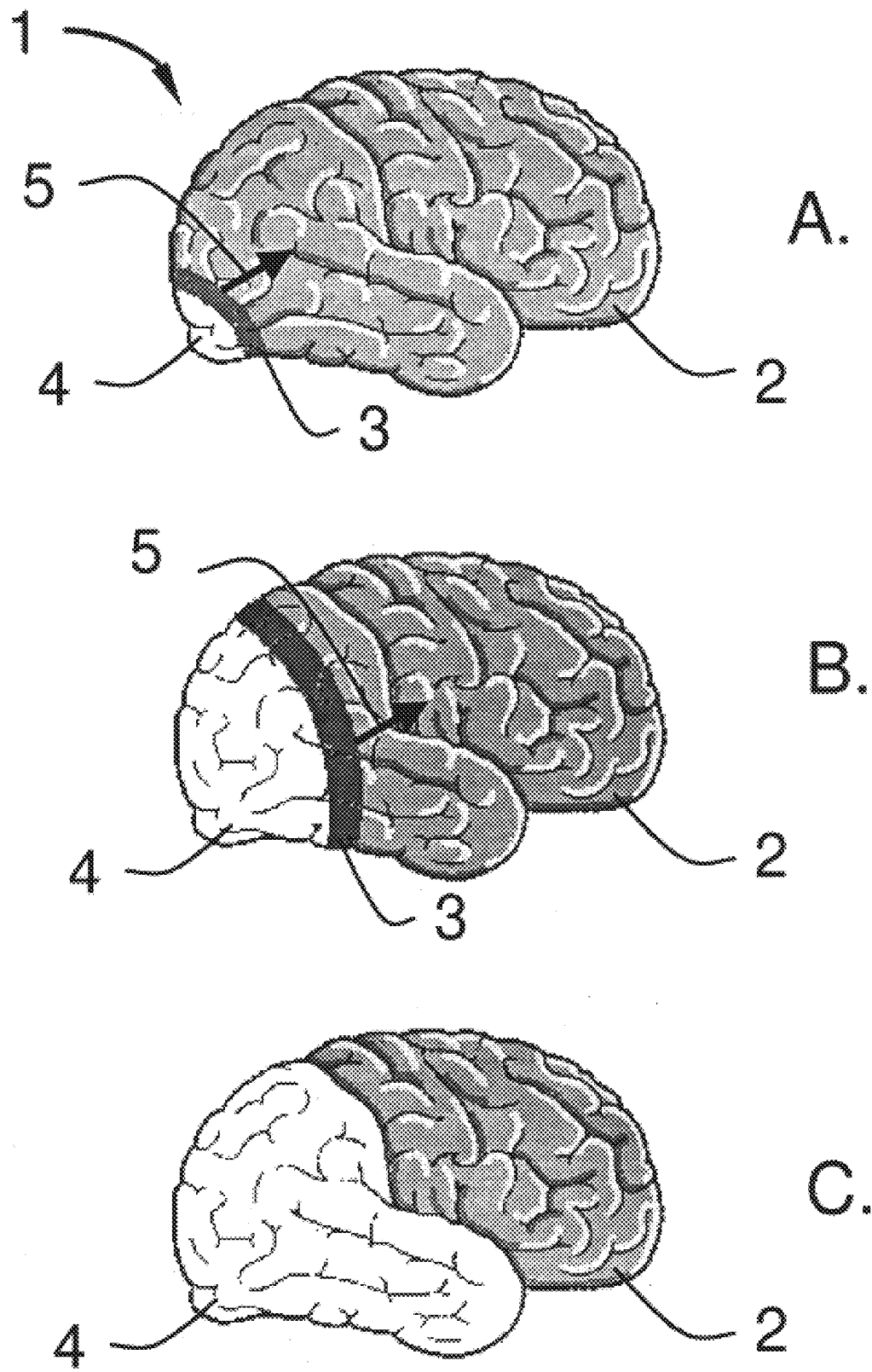
FIG. 1 is an illustration of how a band of excitable neurons spreads across the occipital lobe of a human brain.

FIG. 1 illustrates a time sequence of events associated with a visual aura of a migraine headache. Initially, the brain 1 experiences a band 3 of brain neurons in an excited state. The region 2 of the brain 1 has neurons in a normal state of excitation while the region 4 has neurons that are in depressed state of excitation. As the aura of the migraine headache continues in time, the band 3 shown in FIG. 1A advances at a rate between 2–5 mm per minute in a direction shown by the arrow 5. In FIG. 1B, we see that the band 3 has advanced in an anterior direction, and the region 4 of depressed neurons has become enlarged. Finally in FIG. 1C, we see that the depressed region 4 has spread to occupy a majority of the neurons of the visual cortex (i.e., the occipital lobe). This phenomenon is known as "spreading depression". With a typical patient, the duration during which spreading depression occurs is between 20 and 30 minutes.

Figure 2:
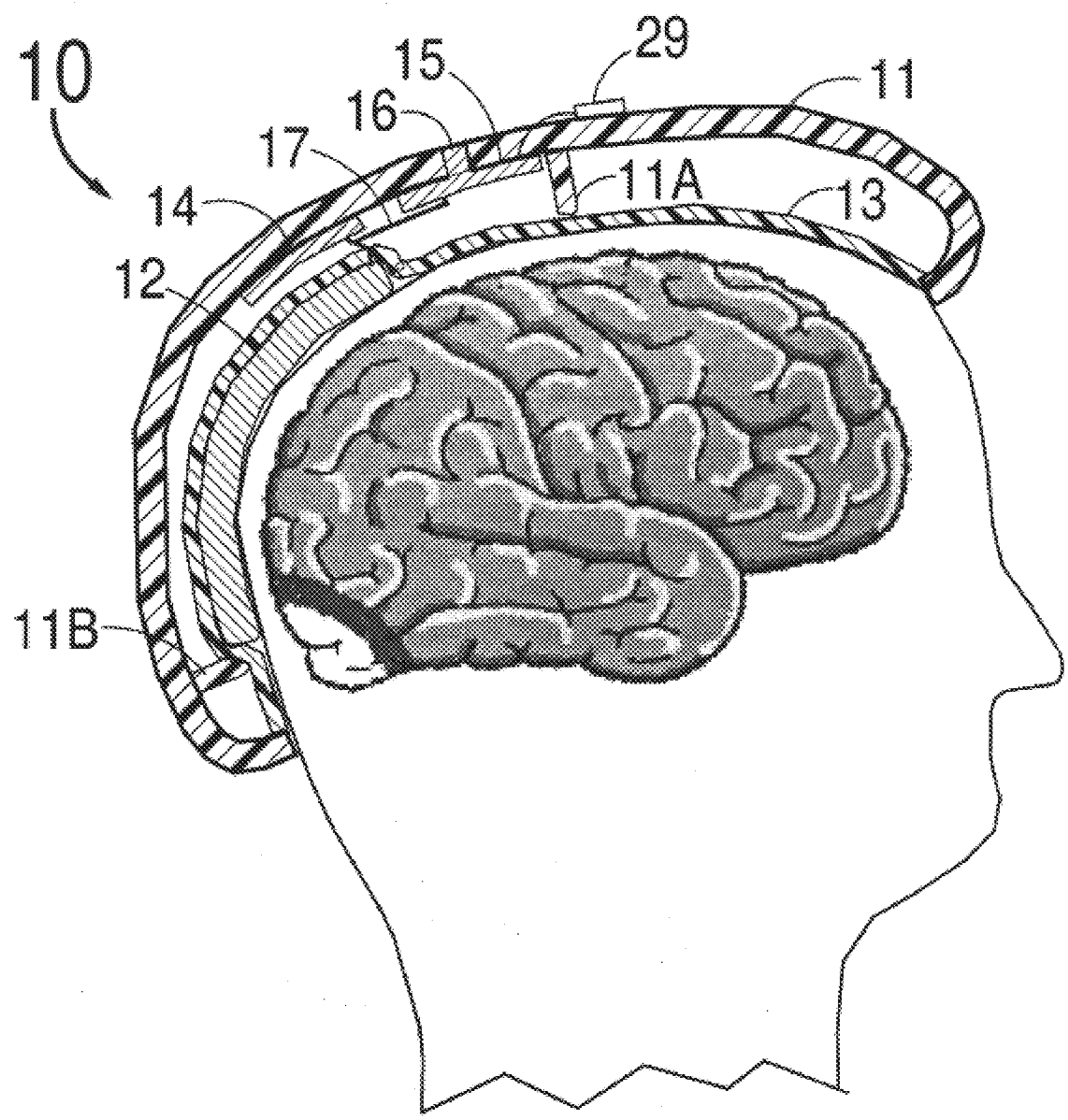
FIG. 2 is a cross section of the present invention showing a magnetic depolarizer system within a helmet on the head of a migraine patient.

FIG. 2 illustrates the head of a migraine patient showing a cross section of the magnetic depolarizer system 10 as it would be contained within a helmet 11 of the type used by bicycle riders. The magnetic depolarizer system 10 consists of a magnetic depolarizer 12, a battery 14, electronic circuitry 15, a recharging receptacle 16 and interconnecting wires 17. The magnetic depolarizer system 10 is contained within the helmet 11 by means of an elastic support 13 that passes between a front support 11A and a rear support 11B. The purpose of the elastic support 13 is to keep the magnetic depolarizer coil 12 in comparatively tight contact with the top and back of the patient's head and at a specific location relative to the patient's cerebral cortex.

Figure 3A:
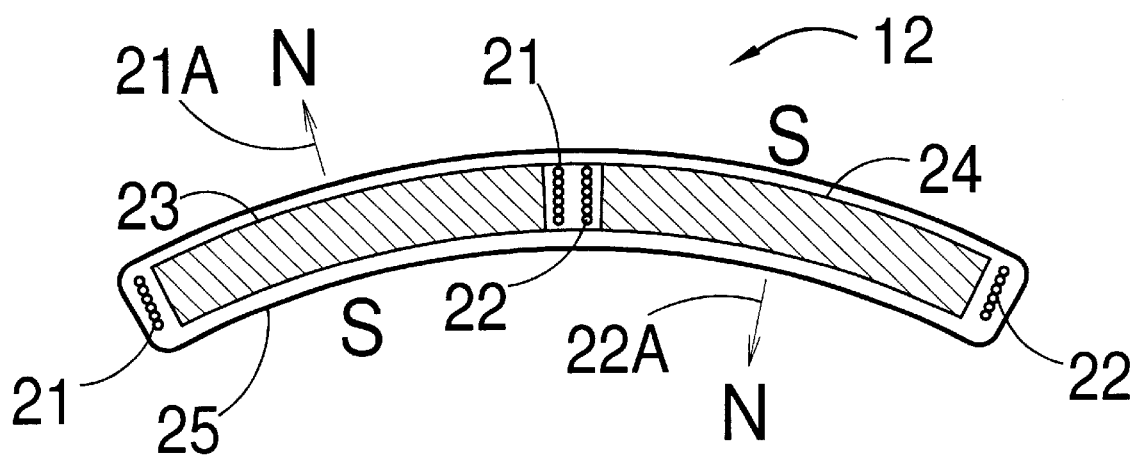
FIG. 3A is a longitudinal cross section of the magnetic depolarizer.

FIG. 3A is a longitudinal cross section of the magnetic depolarizer 12 of FIG. 1. The magnetic depolarizer 12 consists of a first coil 21 placed into a figure-eight configuration with a second coil 22. The two coils 21 and 22 are electrically connected in series in such a way as to create north magnetic poles 21A and 22A in essentially opposite directions when electric current is flowing through the coils 21 and 22. This orientation of coils 21 and 22 can produce a comparatively strong magnetic field onto the cortex of the brain for a distance of a few centimeters beneath the cranium. If the magnetic field changes rapidly in time, it produces an electric current in the visual cortex that can cause the advancing band 3 (of FIG. 1) of excited neurons (or neurons in front of the advancing band) to be depolarized thus preventing the spreading depression phenomenon from continuing. If the spreading depression can be halted, it is likely that at least some migraine patients will not develop a migraine headache or possibly the headache will be less severe.

Because the helmet 11 containing the magnetic depolarizer system 10 can be kept in reasonably close proximity to the patient at all times, it would be reasonable to assume that the patient can place the helmet 11 appropriately in less than the 20 to 30 minutes that is the time period during which the pre-migraine aura occurs. It should also be understood that the patient could use one or more elastic bands (without a helmet) to place the magnetic depolarizer at an appropriate location onto his or her head. A helmet or elastic band(s) or any similar device can be considered a positioner for placing a magnetic depolarizer system onto the head of a human being.

Figure 3B:
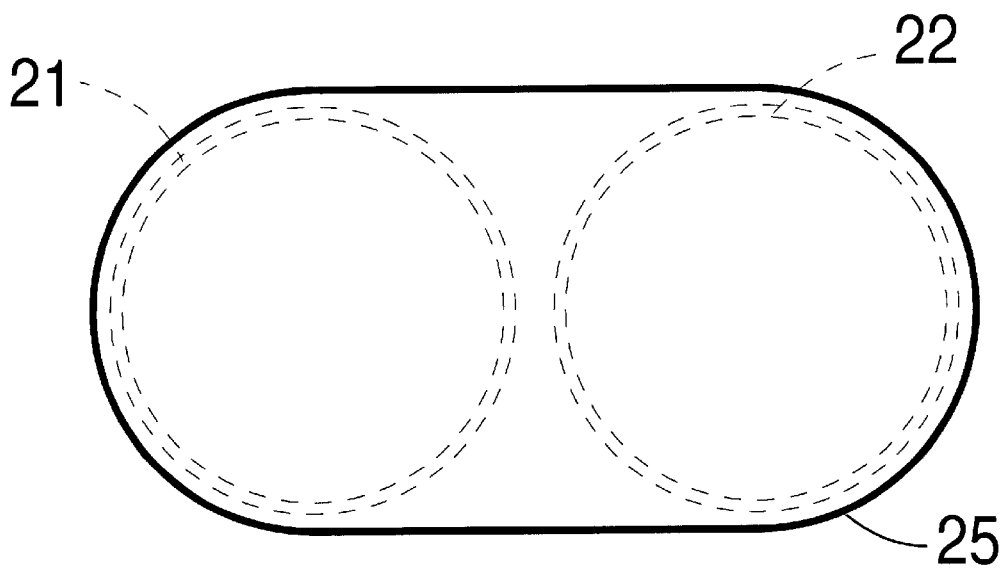
FIG. 3B is a top view of the magnetic depolarizer.

FIG. 3B is a top view of the magnetic depolarizer 12 showing as dotted lines the outline of the coils 21 and 22. In both FIGS. 3A and 3B, it is shown that the coils 21 and 22 could be encapsulated into a plastic housing 25. Furthermore, FIG. 3A shows a magnetic core 23 in the coil 21 and a separate magnetic core 24 in the coil 22. These cores 23 and 24 are not required for the device to perform its intended purpose of generating a depolarizing electric current within the cerebral cortex, but they could be used to provide the same magnetic field intensity in the brain at a lower level of electric current in the coils 21 and 22. To be effective at the high frequency of the magnetic pulses that are used to stimulate the cortex, the cores 23 and 24 would typically be formed from powdered iron or equivalent ferromagnetic material that has low eddy current and hysteresis losses.

Although FIGS. 3A and 3B show a race-track, figure eight type of design for the magnetic depolarizer 12, it should be understood that a simple cylindrical coil (and other shaped coils as well) with or without a ferromagnetic core could be used generate the desired time-varying magnetic field.

Figure 4:
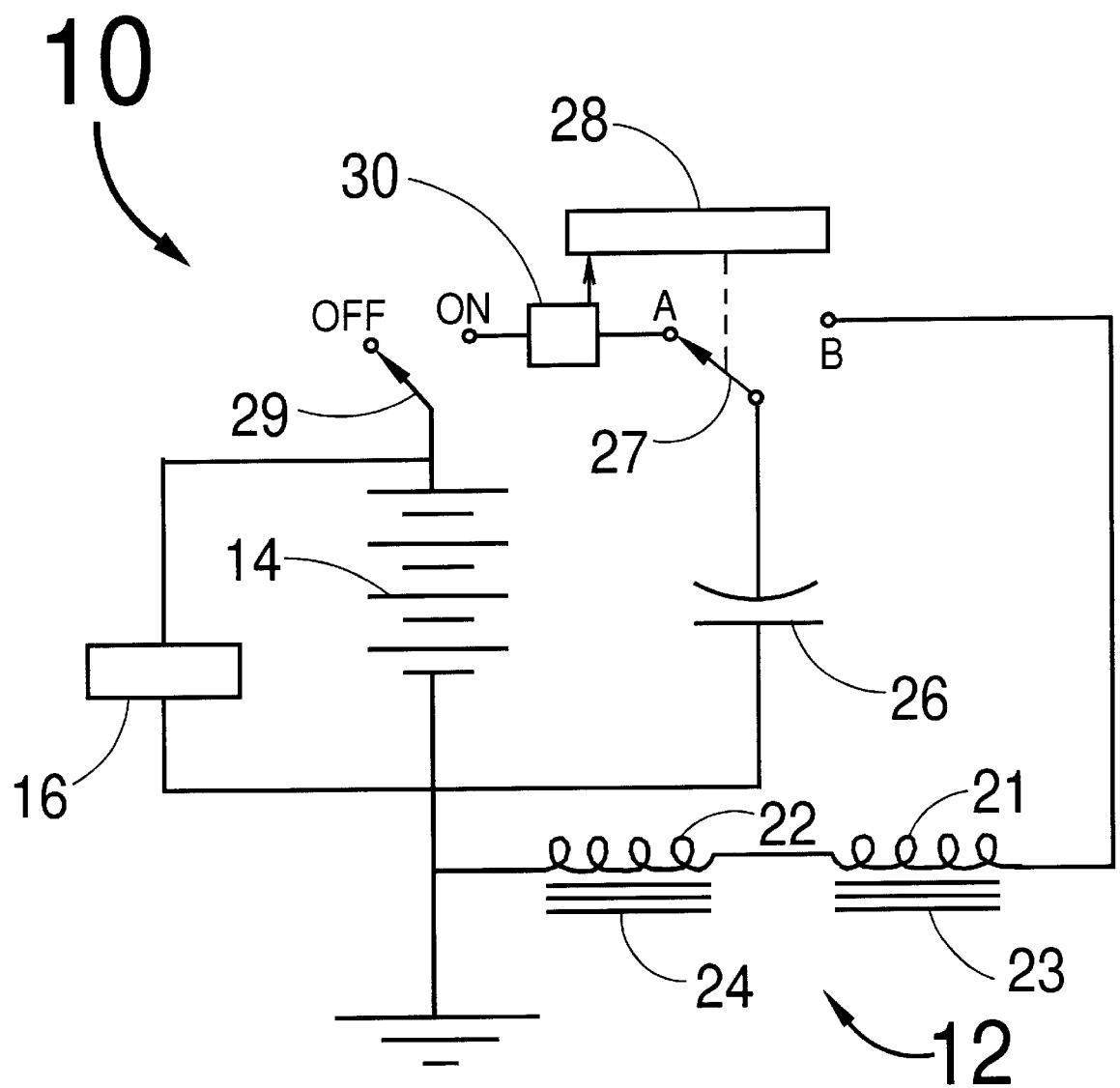
FIG. 4 is a simplified circuit diagram of the main components of a magnetic depolarizer system.

FIG. 4 is a simplified electrical diagram of the magnetic depolarizer system 10. The rechargeable battery 14 can be recharged through the receptacle 16 that can receive a plug from a conventional A-C adapter (not shown) that connects to a-c line voltage (e.g., 115 volts) and delivers an appropriate d-c voltage to recharge the rechargeable battery 14. An adapter for utilizing a car or boat 12 volt battery for operating the magnetic depolarizer system 12 is also envisioned. When the patient is experiencing an aura of a migraine headache, he or she can throw the ON-OFF switch 29 to the ON position. That would cause the d-c to d-c converter 30 to come on and generate a high voltage for rapidly charging the capacitor 26. When the control circuitry 28 senses that the appropriate voltage has been reached, it moves the switch 27 from position A to position B thus discharging the capacitor 26 through the coils 21 and 22 of the magnetic depolarizer 12. As previously described, the coils 21 and 22 could have air cores or they could use magnetically permeable cores 23 and 24. The control circuitry 28 can be used to set the repetition rate for causing magnetic pulses to be delivered. For example, a pulse from the capacitor might last for 70 microseconds and could be repeated at a frequency rate between 0.1 and 100 Hz. A frequency of 1.0 Hz has been shown to be effective in depolarizing brain neurons and may be ideal for some migraine patients. However, other patients might find other repetition rates to be more effective. It is even possible that a single magnetic pulse having a time duration between 10 and 1,000 microseconds could be used to stop an aura thereby preventing the occurrence of a migraine headache.

Although FIGS. 2 and 4 show a battery operated magnetic depolarizer system 10, the system 10 could be operated by plugging into a receptacle at (typically) 115 or 230 volts a-c. Such a system might or might not use a battery as part of its circuitry.

It should be understood that in order to be useful to a migraine patient, the magnetic depolarizer system 10 must have several distinct characteristics that are different from currently available systems for repetitive Transcranial Magnetic Stimulation (rTMS). Specifically, the inventive concept of the present invention includes the fact that the magnetic depolarizer system 10 is readily portable, has preset operating parameters that are not adjustable by the patient, can be placed on the patient's head by the patient and is turned on and off by the patient. "Readily portable" can be defined as having a weight of less than 15 kg. The only presently known rTMS equipment (the Cadwell MES-10) is operated by a physician and not by a patient, has operational parameters that are adjustable by the physician as it is being used (i.e., the parameters are not preset), has a magnetic coil that is placed on a patient by an attending physician, and since the entire system weighs 34 kg it is certainly not readily portable so as to be with the patient wherever he or she might need it. To be useful for its intended purpose, the magnetic depolarizer system 10 would have operating parameters that are preset by an attending physician. These operating parameters can include one or more of the following attributes: the peak intensity of the magnetic field at a distance of 1.0 cm beneath the magnetic depolarizer; the time period of each magnetic pulse; the repetition rate of the magnetic pulses; the total number of pulses to be delivered when the magnetic depolarizer system is turned on; and the location of the magnetic depolarizer within a helmet into which the magnetic depolarizer is placed. Once these parameters are set, the patient would operate the system 10 by placing it on his or her head and then turning the system on and then off after the aura of a migraine headache has been terminated. It may be desirable for the patient to turn the system on but a timer would automatically turn the system off after a preset period of time.

Since the aura of a migraine headache might occur at any time, and since the patient may have only 20 minutes to use the magnetic depolarizer system 10, each patient would want to have a system in relatively close proximity. For example, the patient would want to have the system at home, and/or at work, and/or in his or her car. The magnetic depolarizer system would optimally be sufficiently portable to be taken with the patient on a vacation or on a business trip.

It is also envisioned that the magnetic depolarizer system could include a memory for recording various parameters of the magnetic depolarizer system including the setting of the magnetic field intensity. Within a limited range, it is envisioned that the patient could set different levels for the magnetic field intensity in order to determine that level that is most effective in preventing a migraine headache. It is further envisioned that the magnetic depolarizer system as described herein could be used for the treatment of other disorders such as depression, pain, epilepsy, bi-polar disease and other disorders of the brain.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A magnetic depolarizer system for the treatment of migraine headache, the system including:

a readily portable magnetic depolarizer adapted for placement by a human patient at a specific location on his or her head, the specific location being a region where the application of a time varying magnetic field will decrease the intensity and/or duration of a migraine headache, the magnetic depolarizer having at least one electromagnetic coil that is capable of providing the time varying magnetic field with a peak intensity at some portion of the patient's cerebral cortex of at least 0.1 Tesla;

electrical circuitry connected to the magnetic depolarizer for providing an electrical current through the at least one electromagnetic coil, the electrical circuitry also including a patient operated switch for turning on the magnetic depolarizer system; and, a positioner adapted for placement of the magnetic depolarizer system by the human patient onto the specific location of his or her head.

2. The system of claim 1 wherein the electrical circuitry of the magnetic depolarizer system includes a battery.

3. The system of claim 2 wherein the battery is rechargeable.

4. The system of claim 1 wherein the magnetic depolarizer utilizes two coils, in a race-track, figure-eight configuration.

5. The system of claim 1 wherein the magnetic depolarizer utilizes ferromagnetic cores to decrease the amount of electric current required to provide a specific magnetic field intensity.

6. The system of claim 1 wherein the electronic circuitry is adapted to deliver at least one time varying magnetic pulse.

7. The system of claim 6 wherein the length of the magnetic pulse is between approximately 1 microsecond and approximately 1,000 microseconds.

8. The system of claim 6 wherein the electronic circuitry is adapted to deliver a sequence of pulses comprising a plurality of time varying magnetic pulses, and wherein the magnetic pulses are delivered at a rate of between approximately 0.1 Hz and approximately 1,000 Hz.

9. The system of claim 8 wherein the sequence of pulses is delivered over a time period of between approximately 0.1 second and approximately 100 seconds.

10. The system of claim 1 wherein the positioner comprises a headgear adapted to accurately place the magnetic depolarizer at a specific location on the head of the human being.

11. The system of claim 10 wherein the headgear comprises a helmet of the type worn by bicycle riders.

12. The system of claim 10 wherein the headgear comprises at least one elastic band.

13. The system of claim 1, wherein the electrical circuitry also includes at least one operating parameter that is preset by a physician.

14. A magnetic depolarizer system for the treatment of a migraine headache of a human patient, the system including:

a readily portable magnetic depolarizer adapted for placement by the human patient at a specific location on his or her head, the specific location being a region where the application of a time varying magnetic field will decrease the intensity and/or duration of a migraine headache, the magnetic depolarizer being capable of providing the time varying magnetic field with a peak intensity at some portion of the patient's cerebral cortex of at least 0.1 Tesla; and a patient-operated switch for activating the magnetic depolarizer, the switch being attached to the magnetic depolarizer at a position where it is readily operable by the human patient.

15. A method for the treatment of migraine headaches, the method comprising the following steps:

(a) sensing of an aura of a migraine headache by a migraine patient; and (b) placing a magnetic depolarizer onto the head of the patient at a location where the magnetic depolarizer can create depolarization of the neurons that are the cause of the aura.

16. The method of claim 15 further comprising the step of turning the magnetic depolarizer on so as to create at least one alternating magnetic field pulse onto the patient's cerebral cortex.

17. The method of claim 15 further comprising the step of applying magnetic pulses at a rate between approximately 0.1 Hz and approximately 1,000 Hz.

18. The method of claim 15 further comprising the step of applying a sequence of magnetic pulses for a time period between approximately 0.1 second and approximately 100 seconds.

19. The method of claim 15 further comprising the step of applying at least one magnetic pulse having a duration between approximately 10 microseconds and approximately 1,000 microseconds.

20. The method of claim 15 further comprising the step of powering the magnetic depolarizer by means of a rechargeable battery.

21. The method of claim 15 further comprising the step of turning an ON-OFF switch by the patient first to the ON position and then to the OFF position.

22. The method of claim 15 further comprising the step of having the patient turn the ON-OFF switch to the ON position and then having the magnetic depolarizer system automatically turn the system off after a preset time period.

23. The method of claim 15 further comprising the step of having a physician set at least one operating parameter of the system.

24. A method for treating a migraine headache in a human patient with a readily portable magnetic depolarizer, the method including the steps of:

detecting an occurrence of an onset of a migraine headache by the human patient;

having the human patient place the magnetic depolarizer onto his or her head;

activating the magnetic depolarizer by having the human patient turn on the magnetic depolarizer using a switch that is attached to the magnetic depolarizer; and generating a time-varying magnetic field having a peak intensity at some portion of the patient's cerebral cortex of at least 0.1 Tesla.

25. The method of claim 24, wherein the step of detecting an occurrence of an onset of a migraine headache comprises receiving an input from the patient.

* * * * *